(12) United States Patent
Niinobe et al.

(10) Patent No.: US 7,572,379 B2
(45) Date of Patent: Aug. 11, 2009

(54) REMOVAL OF METAL IONS FROM ONIUM HYDROXIDES AND ONIUM SALT SOLUTIONS

(75) Inventors: Takao Niinobe, Nara (JP); Wilfred Wayne Wilson, Bastrop, TX (US)

(73) Assignee: SACHEM, Inc., Austin, TX (US)

( * ) Notice: Subject to any disclaimer, the term of this patent is extended or adjusted under 35 U.S.C. 154(b) by 963 days.

(21) Appl. No.: 11/223,247

(22) Filed: Sep. 2, 2005

(65) Prior Publication Data
US 2007/0051627 A1 Mar. 8, 2007

(51) Int. Cl.
B01D 15/36 (2006.01)
B01J 39/08 (2006.01)

(52) U.S. Cl. ............... 210/660; 210/681; 210/687; 210/688

(58) Field of Classification Search ............. 210/660, 210/681, 687, 688
See application file for complete search history.

(56) References Cited

U.S. PATENT DOCUMENTS

| | | | |
|---|---|---|---|
| 4,193,968 A | 3/1980 | Sullivan et al. | |
| 4,450,057 A | 5/1984 | Kelly | |
| 4,830,837 A | 5/1989 | Justice et al. | |
| 4,861,490 A | 8/1989 | Morris | |
| 4,966,764 A | 10/1990 | Reed et al. | |
| 5,273,726 A | 12/1993 | Cheresnowsky et al. | |
| 5,439,564 A | 8/1995 | Shimizu et al. | |
| 5,545,309 A | 8/1996 | Shimizu et al. | |
| 5,665,783 A * | 9/1997 | Katzakian et al. ............. 521/26 |
| 5,973,096 A | 10/1999 | Watabe et al. | |
| 6,350,420 B1 | 2/2002 | Duyvesteyn et al. | |
| 6,426,008 B2 | 7/2002 | Silva et al. | |
| 6,508,940 B1 | 1/2003 | Niinobe | |
| 6,746,592 B1 | 6/2004 | Mok et al. | |

FOREIGN PATENT DOCUMENTS

CA 2193778 12/1996

OTHER PUBLICATIONS

International Search Report and Written Opinion, Application No. PCT/US2006/033621, mailed Feb. 13, 2007.

(Continued)

*Primary Examiner*—Arun S Phasge
(74) *Attorney, Agent, or Firm*—Renner, Otto, Boisselle & Sklar, LLP (57) ABSTRACT

The present invention relates to a process for removing dissolved metal ions from an onium hydroxide and/or salt solution, including providing a weak acid ion exchange medium; providing a solution comprising magnesium ions; forming a magnesium-loaded ion exchange medium by contacting the ion exchange medium with the solution comprising magnesium ions; contacting the magnesium-loaded ion exchange medium with an onium hydroxide and/or salt solution containing a first quantity of dissolved metal ions, wherein at least a portion of the dissolved metal ions are removed from the onium hydroxide and/or salt solution; and collecting the onium hydroxide and/or salt solution after the contacting, wherein the solution collected contains a second quantity of dissolved metal ions smaller than the first quantity. The onium hydroxide and/or salt may be tetramethylammonium hydroxide and/or salt, and the metal content may be reduced to about 1 part per billion or less by the process.

33 Claims, 1 Drawing Sheet

OTHER PUBLICATIONS

Sugawara et al.; "A Study on Reclaimed Photoresist Developer Using an Electrodialysis Method"; Extended Abstracts of The International Conference on Solid State Devices and Materials, Japan Society of Applied Physics. Tokyo, JP, vol. 2001, Sep. 26, 2001, pp. 18-19, XP001074474.

Kumbhar et al.; "Removal of Idium Turbidity from Water Using a Magnesium Ion Loaded Weak Acid Cation Exchanger and Fibrous Graphite Electrode"; Separation Science and Technology, vol. 38, No. 9, pp. 2107-2120, 2003.

Meyers; "Applications of Weak Acid Cation Resin in Waste Treatment"; Presented at AESF Conference, Jun. 1999.

* cited by examiner

Fig. 1

REMOVAL OF METAL IONS FROM ONIUM HYDROXIDES AND ONIUM SALT SOLUTIONS

TECHNICAL FIELD

The present invention relates to removal of trace amounts of metal ions such as aluminum from onium hydroxide and/or onium salt solutions.

BACKGROUND

Onium hydroxides, such as tetramethylammonium hydroxide, are used in semiconductor processes. Such onium hydroxides are required to be of extremely high purity. For example, the SEMI C46-0699 specification for aluminum ion requires that the aluminum content be less than 10 part per billion (ppb) in 25% tetramethylammonium hydroxide.

Environmental and economic concerns drive the desire to recycle materials, including materials such as the onium hydroxides used in semiconductor processes. Materials such as onium hydroxides and onium salts are the subject of rather stringent environmental regulations. The production of new onium hydroxides and onium salts is more expensive than is the recycling of used onium hydroxides and onium salts. However, use of materials such as onium hydroxides in semiconductor processing inevitably contaminates the onium hydroxides with materials such as aluminum and other metal ions. While removal of most metal ions, including aluminum, down to levels in the part per million (ppm) range has been known, it has proven quite difficult to remove metals such as aluminum to levels near and below 1 ppb. In order to meet this specification, it has been generally necessary to simply start with new onium hydroxide material, since it has been impossible to attain such low levels of metal ions in recycled onium hydroxide solutions. Thus, it has been difficult to recycle materials such as the onium hydroxides used in semiconductor processing for re-use in semiconductor processing. Removal of metals such as aluminum from recycled onium hydroxide and salt solutions has been a long-standing problem, and a need remains for such methods, if materials such as onium hydroxides and salts are to be successfully and economically recycled for use in the most demanding applications, such as in semiconductor processing.

SUMMARY

The present invention provides a solution to the problem of recycling onium hydroxide solutions while attaining metal ion contents acceptable for re-use of the recovered onium hydroxide or salt solutions in the most demanding applications.

In accordance with one embodiment of the present invention, there is provided a process for removing dissolved metal ions from an onium hydroxide and/or salt solution, comprising:

providing a weak acid ion exchange medium;
providing a solution comprising magnesium ions;
forming a magnesium-loaded ion exchange medium by contacting the ion exchange medium with the solution comprising magnesium ions;
contacting the magnesium-loaded ion exchange medium with an onium hydroxide and/or salt solution containing a first quantity of dissolved metal ions, wherein at least a portion of the dissolved metal ions are removed from the onium hydroxide and/or salt solution; and
collecting the onium hydroxide and/or salt solution after the contacting, wherein the solution collected contains a second quantity of dissolved metal ions smaller than the first quantity.

In accordance with another embodiment of the present invention, there is provided a process for recycling a recovered tetramethylammonium hydroxide solution containing dissolved metal ions, comprising:

providing a weak acid ion exchange medium;
providing a solution comprising magnesium ions;
forming a magnesium-loaded ion exchange medium by contacting the ion exchange medium with the solution comprising magnesium ions;
contacting the magnesium-loaded ion exchange medium with a recovered tetramethylammonium hydroxide and/or salt solution containing a first quantity of dissolved metal ions, wherein at least a portion of the dissolved metal ions are removed from the tetramethylammonium hydroxide and/or salt solution; and
collecting a tetramethylammonium hydroxide and/or salt solution, wherein the collected solution contains a second quantity of dissolved metal ions smaller than the first quantity.

In accordance with another embodiment of the present invention, there is provided a process for recycling a recovered tetramethylammonium hydroxide and/or salt solution containing dissolved metal ions, comprising:

providing a carboxylate weak acid ion exchange medium and loading the ion exchange medium onto a column;
providing a solution comprising magnesium ions;
forming a magnesium-loaded ion exchange medium by contacting the ion exchange medium with the solution comprising magnesium ion, wherein the solution comprising magnesium ions passes through the column in a first direction;
rinsing the ion exchange medium by contacting the magnesium-loaded ion exchange medium with a substantially metal-free tetramethylammonium hydroxide and/or salt solution, wherein the substantially metal-free tetramethylammonium hydroxide and/or salt solution passes through the column in a second direction opposite to the first direction;
contacting the rinsed magnesium-loaded ion exchange medium with the recovered tetramethylammonium hydroxide and/or salt solution, wherein the recovered tetramethylammonium hydroxide and/or salt solution passes through the column in the second direction, wherein at least a portion of the dissolved metal ions are retained on the ion exchange medium; and
collecting the tetramethylammonium hydroxide and/or salt solution after the contacting, wherein the solution collected contains a reduced quantity of dissolved metal ions.

In accordance with the foregoing embodiments of the processes of the present invention, metal ion contents less than about 1 ppb can be obtained in recycled onium hydroxide and/or salt solutions.

Thus, the present invention addresses the problem of recycling onium hydroxide and salt solutions to provide recycled high purity onium hydroxide and salt solutions containing levels of metals such as aluminum at concentrations acceptable for use of the recycled materials in demanding uses, such as semiconductor processing.

It should be appreciated that the process steps and structures described herein may not provide a complete system or process flow for carrying out a recycling process for onium hydroxide and/or salt solutions, such as would be used in a recycling facility for such materials. The present invention may be practiced in conjunction with techniques and apparatus currently used in the art, and only so much of the commonly practiced materials, apparatus and process steps are included as are necessary for an understanding of the present invention.

DETAILED DESCRIPTION

As noted, the present invention relates to a process for purifying an onium hydroxide and/or onium salt solution, and in particular, for reducing the metal content of onium hydroxide and/or salt solutions. The onium hydroxide and/or onium salt solutions applied to the present process may be recovered from, e.g., semiconductor processing and from other processes which include the use of onium hydroxide and/or salt solutions. In one embodiment, the present invention is applicable to onium hydroxide solutions. In one embodiment, the present invention is applicable to onium salt solutions. In one embodiment, the onium salts may be converted to onium hydroxides, and the onium hydroxides purified by processes known to those of skill in the art. Such conversion processes include those disclosed in the present applicant's U.S. Pat. No. 6,508,940, as well as in commonly assigned U.S. Pat. Nos. 6,787,021; 6,217,743; 6,207,039; 5,968,338; 5,951,845; 5,910,237; 5,868,916; 5,853,555; and 5,833,832, the disclosure of each of which is incorporated herein by reference for the teachings relating to conversion of onium salts into onium hydroxides and to purification of the onium hydroxides by various methods. While those processes and disclosures relate to conversion and purification of onium hydroxides, the present invention primarily relates to recycling such onium hydroxide and/or onium salt solutions, and in particular to reducing the metal ion content of the recycled onium hydroxide and/or onium salt solutions to levels acceptable for re-use of the recycled onium hydroxide and/or onium salt solutions in the most demanding industries, such as the semiconductor industry. In one embodiment, the present invention is applicable to mixtures of onium hydroxides and salts in a solution, thus the reference to onium hydroxide "and/or" salt, in this disclosure.

Organic Onium Hydroxides and Onium Salts

In one embodiment, the onium hydroxide and/or salt solution may comprise an organic onium hydroxide and/or organic onium salt. Suitable organic onium hydroxides and salts for the present invention include organic onium hydroxides such as quaternary ammonium hydroxides, quaternary phosphonium hydroxides, tertiary sulfonium hydroxides, tertiary sulfoxonium hydroxides and imidazolium hydroxides, and the corresponding salts. Herein, any reference to "onium hydroxide and/or salt" refers to either or both of organic onium hydroxide and/or organic onium salt, unless clearly, specifically limited to one or the other.

In the following description of exemplary onium hydroxides and onium salts, the specific embodiments shown below are the hydroxides. It is to be understood that in the following disclosure, unless specifically limited to onium hydroxides, the corresponding onium salts are included. Those of ordinary skill in the art will understand that the onium salt may be determined based on the disclosure relating to the onium hydroxides, with appropriate adjustments for the charge on the anion forming the onium salt. That is, where the salt is formed from a singly charged onium ion (cation) and a singly charged anion, such as a halide, there will be a single onium ion for each anion, and where the salt is formed from a singly charged onium ion and a doubly charged anion, such as a sulfate, $SO_4^=$, there will be two onium ions for each doubly charged anion.

Suitable anions for the onium salts include anions of common acids. Such anions include, for example, a halide ion, a sulfate, hydrogen sulfate or alkylsulfate anion, a carboxylate anion, a nitrate anion, a carbonate, bicarbonate or alkyl carbonate anion, a phosphate, hydrogen phosphate or dihydrogen phosphate anion, a sulfonate anion, an alkylsulfonate anion, etc. Most often the anion will be a halide, and more often, chloride. Thus, in one embodiment, in the following structures, the OH group can be replaced with an "X" group, where the X represents the anion, and "x" is may be a non-integral value, such as ½ or ⅓. In another embodiment, the number of onium moieties can be selected to balance an integral number of "X" groups as needed to obtain a balanced, neutral salt.

In one embodiment, the onium hydroxides may generally be characterized by the formula I:

$$A(OH)_x \quad (I)$$

wherein A is an onium group and x is an integer equal to the valence of A. Examples of onium groups include ammonium groups, phosphonium groups, sulfonium, sulfoxonium and imidazolium groups. As noted above, a suitable anion may be substituted for the hydroxide, to form the corresponding onium salt.

In one embodiment, the quaternary ammonium hydroxides and salts and quaternary phosphonium hydroxides and salts may be characterized by the formula II:

wherein A is a nitrogen or phosphorus atom, $R^1$, $R^2$, $R^3$ and $R^4$ are each independently alkyl groups containing from 1 to about 20, or 1 to about 10 carbon atoms, hydroxyalkyl or alkoxyalkyl groups containing from 2 to about 20, or 2 to about 10 carbon atoms, substituted or unsubstituted aryl groups or hydroxyaryl groups containing from 6 to 18 ring carbon atoms, or $R^1$ and $R^2$ or $R^3$ together with A may form a heterocyclic group provided that if the heterocyclic group contains a C=A group, $R^3$ is the second bond. As noted above, in the case of the onium salts, the OH⁻ group is replaced with a suitable anion.

The alkyl groups $R^1$ to $R^4$ may be linear or branched, and specific examples of alkyl groups containing from 1 to 20 carbon atoms include methyl, ethyl, propyl, butyl, pentyl, hexyl, heptyl, octyl, isooctyl, nonyl, decyl, isodecyl, dodecyl, tridecyl, isotridecyl, hexadecyl and octadecyl groups. $R^1$, $R^2$, $R^3$ and $R^4$ also may be hydroxyalkyl groups containing from 2 to 5 carbon atoms such as hydroxyethyl and the various isomers of hydroxypropyl, hydroxybutyl, hydroxypentyl, etc. In one embodiment, $R^1$, $R^2$, $R^3$ and $R^4$ are independently alkyl and/or hydroxyalkyl groups containing 1 to about 5 carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups. The aryl or hydroxyaryl groups may be substituted with, e.g., $C_1$-$C_{20}$ alkyl groups. Most often, $R^1$ to $R^4$ are lower alkyl, such as methyl. As noted above, a suitable anion may be substituted for the hydroxide, to form the corresponding onium salt.

In one embodiment, the quaternary ammonium hydroxides and salts which can be treated in accordance with the process of the present invention may be represented by Formula III:

(III)

wherein $R^1$, $R^2$, $R^3$, $R^4$, and y are as defined in Formula II. In one embodiment, $R^1$-$R^4$ are alkyl and/or hydroxyalkyl groups containing from 1 to about 5 carbon atoms. Thus, in one embodiment, the ammonium hydroxide and/or salt comprises a tetraalkylammonium hydroxide. Specific examples of ammonium hydroxides include tetramethylammonium hydroxide (TMAH), tetraethylammonium hydroxide (TEAH), tetrapropylammonium hydroxide, tetrabutylammonium hydroxide, tetra-n-octylammonium hydroxide, methyltriethylammonium hydroxide, diethyldimethylammonium hydroxide, methyltripropylammonium hydroxide, methyltributylammonium hydroxide, cetyltrimethylammonium hydroxide, trimethylhydroxyethylammonium hydroxide, trimethylmethoxyethylammonium hydroxide, dimethyldihydroxyethylammonium hydroxide, methyltrihydroxyethylammonium hydroxide, phenyltrimethylammonium hydroxide, phenyltriethylammonium hydroxide, benzyltrimethylammonium hydroxide, benzyltriethylammonium hydroxide, dimethylpyrolidinium hydroxide, dimethylpiperidinium hydroxide, diisopropylimidazolinium hydroxide, N-alkylpyridinium hydroxide, etc. In one embodiment, the quaternary ammonium hydroxides used in accordance with this invention are TMAH and TEAH. As noted above, a suitable anion may be substituted for the hydroxide, to form the corresponding ammonium salt.

Examples of quaternary phosphonium hydroxides and salts representative of Formula III wherein A=P which can be employed in accordance with the present invention include tetramethylphosphonium hydroxide, tetraethylphosphonium hydroxide, tetrapropylphosphonium hydroxide, tetrabutylphosphonium hydroxide, trimethylhydroxyethylphosphonium hydroxide, dimethyldihydroxyethylphosphonium hydroxide, methyltrihydroxyethylphosphonium hydroxide, phenyltrimethylphosphonium hydroxide, phenyltriethylphosphonium hydroxide and benzyltrimethylphosphonium hydroxide, etc. As noted above, a suitable anion may be substituted for the hydroxide, to form the corresponding phosphonium salt.

In another embodiment, the tertiary sulfonium hydroxides and salts which can be employed in accordance with the present invention may be represented by the formula IV:

(IV)

wherein $R^1$, $R^2$ and $R^3$ are as defined in Formula II.

Examples of the tertiary sulfonium compounds represented by Formula IV include trimethylsulfonium hydroxide, triethylsulfonium hydroxide, tripropylsulfonium hydroxide, etc. As noted above, a suitable anion may be substituted for the hydroxide, to form the corresponding sulfonium salt.

In another embodiment, the tertiary sulfoxonium hydroxides and salts which can be employed in accordance with the present invention may be represented by the formula V:

(V)

wherein $R^1$, $R^2$ and $R^3$ are as defined in Formula II.

Examples of the tertiary sulfoxonium hydroxides represented by Formula V include trimethylsulfoxonium hydroxide, triethylsulfoxonium hydroxide, tripropylsulfoxonium hydroxide, etc. As noted above, a suitable anion may be substituted for the hydroxide, to form the corresponding sulfoxonium salt.

In another embodiment, the imidazolium hydroxides which can be employed in accordance with the present invention may be represented by the formula VI:

(VI)

wherein $R^1$ and $R^3$ are as defined in Formula II. As noted above, a suitable anion may be substituted for the hydroxide, to form the corresponding imidazolium salt.

Onium hydroxides and onium salts are commercially available. Additionally, onium hydroxides can be prepared from the corresponding onium salts such as the corresponding onium halides, carbonates, formates, sulfates and the like. Various methods of preparation are described in U.S. Pat. Nos. 4,917,781 (Sharifian et al) and 5,286,354 (Bard et al) which are hereby incorporated by reference. There is no particular limit as to how the onium hydroxide or salt is obtained or prepared.

In one embodiment, the organic onium hydroxide comprises one or more of tetramethylammonium hydroxide, tetraethylammonium hydroxide, tetrapropylammonium hydroxide, tetrabutylammonium hydroxide, methyltriphenylammonium hydroxide, phenyltrimethylammonium hydroxide, benzyltrimethylammonium hydroxide, methyltriethanolammonium hydroxide, tetrabutylphosphonium hydroxide, methyltriphenylphosphonium hydroxide, trihexyltetradecylphosphonium hydroxide, tributyltetradecylphosphonium hydroxide, $[(CH_3)_3NCH_2CH(OH)CH_2N(CH_3)_3]^{2+}[OH^-]_2$, 1-butyl-3-methylimidazolium hydroxide, trimethylsulfonium hydroxide, trimethylsulfoxonium hydroxide, trimethyl (2,3-dihydroxypropyl)ammonium hydroxide, $[(C_6H_5)CH_2N(CH_3)_2CH_2CH(OH)CH_2N(CH_3)_2CH_2CH(OH)CH_2N(CH_3)_2\ CH_2—CH(OH)CH_2N(CH_3)_2CH_2(C_6H_5)]^{4+}[OH^-]_4$, and $[(CH_3)_3NCH_2CH(OH)CH_2OH]^+[OH^-]$, and hexamethonium dihydroxide. In one embodiment, the onium hydroxide is benzyltrimethylammonium hydroxide. As noted above, a suitable anion may be substituted for the hydroxide, to form the corresponding onium salt.

The concentration of the onium hydroxide and/or salt in the solutions of the present invention may range up to about 25 wt % or in some cases, higher, of the recycled composition. In one embodiment, the onium hydroxide and/or salt concentration is in a range from about 10 wt % to about 20 wt %, and in another embodiment, the onium hydroxide and/or salt concentration is in a range from about 12 wt % to about 17 wt %, all concentrations based on the total weight of the recycled composition.

Weak Acid Ion Exchange Resin

Suitable weak acid ion exchange resins are commercially available. The present invention is not limited to any particular weak acid ion exchange resin. In general, weak acid ion exchange resins are carboxylate-type resins, in which the "active" sites are carboxyl groups. Experiments suggest that, in general, strong acid ion exchange resins, such as sulfonic acid resins, may be not suitable for use in the present invention. However, it may be possible to use a strong acid ion exchange resin under the appropriate conditions.

In one embodiment, the weak acid ion exchange resin is a polymer of acrylic acid or an alkylacrylic acid, such as methacrylic or ethacrylic acid. Many commercially available weak acid ion exchange resins comprise either polyacrylic acid or polymethacrylic acid or a combination thereof, and are crosslinked with divinylbenzene.

Commercially available weak acid ion exchange media include, for example, LEWATIT® CNP 80 WS or CNP/LF, acrylic based weakly acidic cation exchange resins available from Bayer AG or Sybron Chemicals, Inc.; PUROLITE® C-104E, a weakly acidic ion exchange medium available from The Purolite Company; DIAION® WK10, WK11, WK100, WT01S, which are weakly acidic cation exchange media based on polymethacrylic acid, and WK40, which is a weakly acidic cation exchange media based on polyacrylic acid, available from Mitsubishi Chemical Corp.; and DOWEX® MAC-3, a weak acid polyacrylic cation exchange medium available from The Dow Chemical Co.; and AMBERLITE™ IRC76 weak acid cation exchange resin available from Rohm and Haas. The foregoing are examples of possibly suitable weak acid ion exchange media which may be used in accordance with the present invention, and are not intended to be limiting to the scope of the invention. Additional ion exchange media may be suitably selected by those of ordinary skill in the art.

Magnesium Ion Source

In one embodiment, the magnesium ion source is any magnesium salt or magnesium hydroxide, and in one embodiment, it is $Mg(OH)_2$, magnesium hydroxide. In another embodiment, the source of magnesium ions is MgO, magnesium oxide, which when dissolved in water, forms magnesium hydroxide. Magnesium hydroxide, magnesium oxide and other magnesium compounds are readily commercially available.

Ion Exchange Column

In one embodiment, the ion exchange is carried out in a column, in which the weak acid ion exchange medium is loaded onto a suitable column, as is well known in the art. In one embodiment, the column is vertically oriented to allow for passage of at least some liquid materials through the column by gravity. As will be understood by those of ordinary skill in the art, a pump may also be used in either a downwardly or upwardly flowing column, for example, to increase the flow rate that would be obtained by gravity alone, or for other reasons. As also will be understood, if the column is vertically oriented, to obtain countercurrent flow, i.e., to have the liquid flow upward through the column, a pump or other means may be used. Such other means may include, for example, a reservoir of liquid material held at a position above the column, so that gravity can be used as the driving force for the countercurrent flow of the liquid material up through the column. Any suitable liquid transfer means known in the art may be used.

In one embodiment, the column is formed of a relatively inert or chemically unreactive material. Thus in one embodiment, the column may be fabricated of a glass or in another embodiment of a fluorinated polymer. Fluorinated polymers have excellent resistance to various solvents and chemicals, including organic solvents and strong bases, and may be used. Examples include Teflon®, Avatrel®, polyvinylidene fluoride (PVDF), THV Fluorothermoplastic (Dyneon, St. Paul Minn.), Hostaflon TF 5035 (Dyneon), fluorinated ethylene propylene (FEP), polytetrafluoroethylene (PTFE), and perfluoroalkoxy polymer (PFA), among others. Any suitable material may be selected for use as the column.

As will be recognized, it is not necessary for the column to be oriented in any particular direction or orientation. The column may be vertical, horizontal, coiled or arranged in any suitable way, provided that it can be loaded with the ion exchange medium and that the appropriate liquids can be passed through it.

Process for Removal of Metal Ions Such as Aluminum

Figure 1:
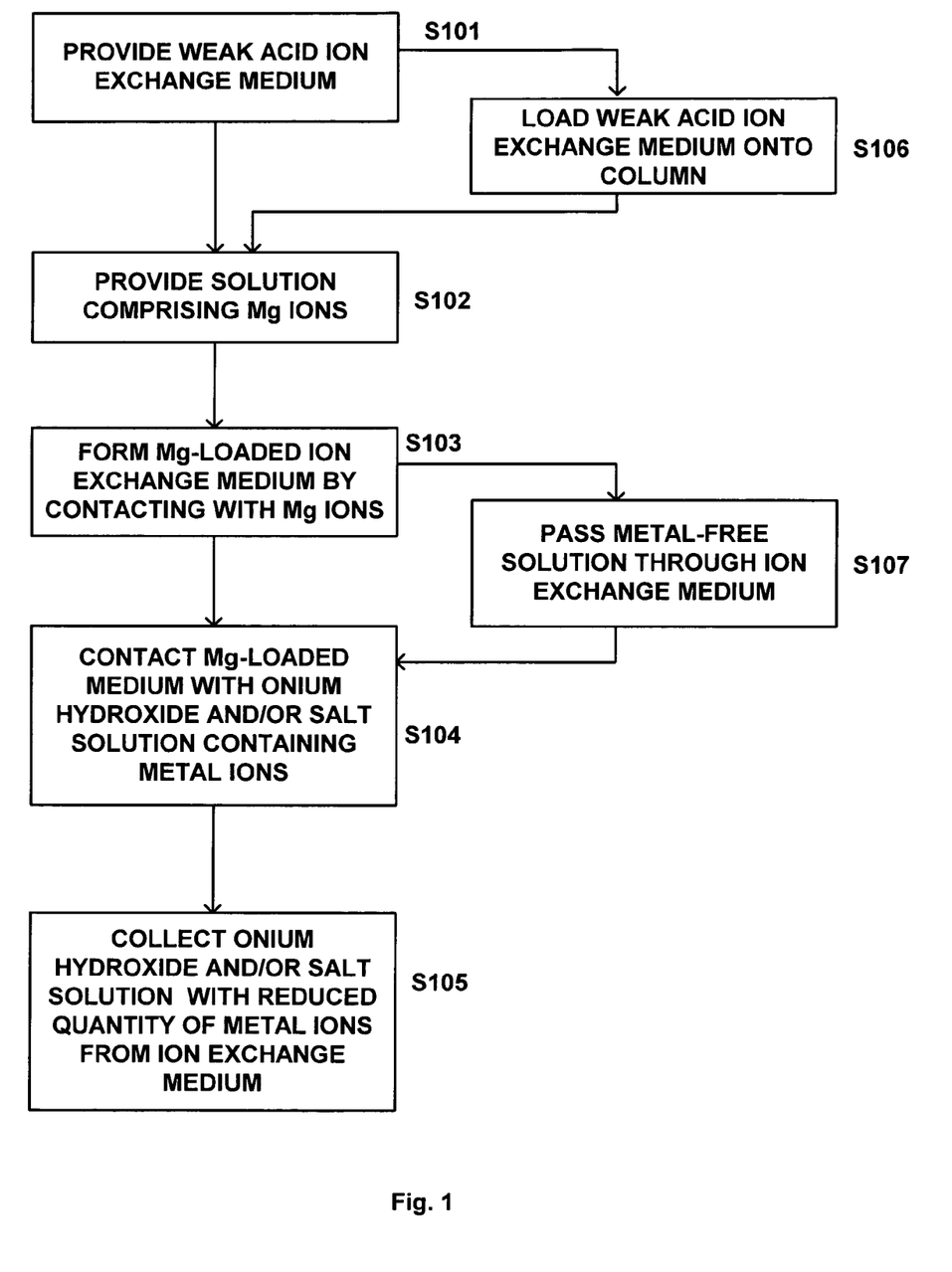
FIG. 1 is a schematic flow diagram illustrating steps of various embodiments of a process in accordance with the invention.

In one embodiment, the present invention relates to a process for removing dissolved metal ions from an onium hydroxide and/or salt solution containing unwanted dissolved metal ions. Referring to FIG. 1, in one embodiment, the process for removing dissolved metal ions from an onium hydroxide and/or salt solution in accordance with the present invention, includes steps of:

providing a weak acid ion exchange medium (FIG. 1, step S101);

providing a solution comprising magnesium ions (FIG. 1, step S102);

forming a magnesium-loaded ion exchange medium by contacting the ion exchange medium with the solution comprising magnesium ions (FIG. 1, step S103);

contacting the magnesium-loaded ion exchange medium with an onium hydroxide and/or salt solution containing dissolved metal ions, wherein at least a portion of the dissolved metal ions are removed from the onium hydroxide and/or salt solution (FIG. 1, step S104) by this contacting; and collecting the onium hydroxide and/or salt solution after the contacting. (FIG. 1, step S105).

In one embodiment, the onium hydroxide and/or salt solution which contacts the magnesium-loaded ion exchange medium contains a first quantity of dissolved metal ions. In one embodiment, the onium hydroxide and/or salt solution collected after the contacting contains a second quantity of dissolved metal ions, and the second quantity is less than the first quantity. In one embodiment, the second quantity is less than about 10 ppb, and in another embodiment, the second quantity is less than about 1 ppb, and in yet another embodiment, the second quantity is not detectable.

In one embodiment, the weak acid ion exchange medium is loaded onto a column (FIG. 1, step S106). As noted, the orientation, shape and configuration of the column is not limited. In one embodiment, the loading of the magnesium ions onto the column is substantially stoichiometric, whereby substantially all of the weak acid sites on the ion exchange medium are occupied by magnesium ions.

In one embodiment, after the magnesium ions are loaded onto the ion exchange medium, the magnesium-loaded ion exchange medium is washed with a metal-free solution of onium hydroxide and/or salt, by passing the metal-free solution through or over the magnesium-loaded ion exchange medium (FIG. 1, step S107). This washing would remove any excess magnesium ions (unbound to the ion exchange medium) or particles of undissolved magnesium hydroxide and would condition the column to the onium hydroxide and/or salt solution to be treated subsequently. Thus, in one embodiment, the process further includes passing a substantially metal ion-free onium hydroxide and/or salt solution over the ion exchange medium after the step of passing the solution comprising magnesium ions through the ion exchange medium and prior to the step of passing the onium hydroxide and/or salt solution through the ion exchange medium. In one embodiment, the substantially metal-free onium hydroxide and/or salt solution contains about 1 part per billion or less of metal ion. In one embodiment, the substantially metal-free onium hydroxide and/or salt solution contains about 0.1 part per billion or less of metal ion. In one embodiment, the substantially metal-free onium hydroxide and/or salt solution contains a quantity of metal ion that is not detectable by standard chemical analysis. In one embodiment, the onium concentration of the substantially metal-free onium hydroxide and/or salt solution is at about the same onium concentration as is the onium hydroxide and/or salt solution to be treated in the process of the present invention.

In addition, if desired, the ion exchange medium may be washed with other solutions as determined by the operator, and this additional washing may be carried out any one or more of (a) either or both prior to or subsequent to the loading of the ion exchange medium with magnesium ions (FIG. 1, step S103); (b) either or both prior to or subsequent to the washing of the ion exchange medium with metal-free solution (FIG. 1, step S107); or (c) either or both prior to or subsequent to the passing of the onium hydroxide and/or salt solution containing dissolved metal ions through the ion exchange medium (FIG. 1, step S104).

As noted above, the magnesium ions may be provided from a variety of sources, two of which are MgO and $Mg(OH)_2$. In one embodiment, the step of providing a solution comprising magnesium ions comprises dissolving the MgO and/or $Mg(OH)_2$ in water. In one embodiment, the magnesium ion solution is in the form of a slurry, due to the relatively low solubility of magnesium ion in water.

In one embodiment, the magnesium ion solution is circulated through the ion exchange medium in a counterflow direction, that is, in a direction substantially opposite to that in which the onium hydroxide and/or salt solution containing dissolved metal ions will be passed through the ion exchange medium. In one embodiment, the magnesium ions are provided by passing a solution comprising the magnesium ions through the ion exchange medium in a first direction and the onium hydroxide and/or salt solution is passed through the ion exchange medium in a second direction opposite to the first direction. In an embodiment in which the ion exchange medium is loaded onto a column, the magnesium ions are provided by passing a solution comprising the magnesium ions through the column in a first direction and the onium hydroxide and/or salt solution is passed through the column in a second direction opposite to the first direction. Although not to be bound by theory, the counter-current procedure for loading the magnesium ions onto the ion exchange medium may avoid loading particulate magnesium oxide or hydroxide on the column, since the subsequent passing of other liquids, e.g., the onium hydroxide and/or salt solution, through the ion exchange medium would remove any particulate magnesium oxide or hydroxide at the effluent end of the ion exchange medium.

As noted above, in one embodiment, the ion exchange medium used in accordance with the present invention is a weak acid ion exchange resin. As is known in the art and discussed above, in general, weak acid ion exchange resins include carboxyl groups, —COOH, as the active ion exchanging moiety. A given ion exchange medium contains a certain quantity of such carboxyl groups per unit of weight or volume. These carboxyl groups may be referred to as available acid sites, for ion exchange.

In one embodiment, a quantity of magnesium ions loaded onto the ion exchange medium is substantially stoichiometric with available acid sites on the ion exchange medium. That is, in one embodiment, in substantially all of the —COOH groups, the $H^+$ ion has been replaced with a magnesium ion. More correctly, as will be recognized, since a magnesium ion carries two positive charges ($Mg^{++}$), the $H^+$ ions on two neighboring —COOH groups are replaced by a magnesium ion. Thus, the exchange reaction would be written as:

and, where the $Mg^{++}$ was provided as $Mg(OH)_2$, the two $H^+$ ions would combine with the 2 $OH^-$ groups to form 2 molecules of water, $H_2O$. Thus, the overall exchange reaction in preparing the ion exchange medium for use in the present invention would be written as:

It is noted that, even if MgO is used as the source of magnesium ions, when this is mixed with water, it will be substantially converted to magnesium hydroxide, $Mg(OH)_2$, so that the same exchange reaction would take place in loading the magnesium ion onto the ion exchange medium.

In one embodiment, the metal ions to be removed include aluminum. In one embodiment, the metal ions to be removed include aluminum, iron and zinc, and alloys or mixtures of any two or more of these. In another embodiment, the metal ions to be removed include aluminum, barium, bismuth, boron, cadmium, calcium, cerium, copper, germanium, hafnium, iron, lanthanum, lead, nickel, niobium, scandium, silicon, strontium, titanium, tungsten, yttrium, zinc, zirconium, and alloys or mixtures of any two or more of these. In one embodiment, the metal ions to be removed include any of the metals commonly used in semiconductor processing and devices.

The exact mechanism by which the magnesium-loaded ion exchange medium removes the metal ions from the recycled onium hydroxide and/or salt solution is not fully known. Although not to be bound by theory, it is believed that it is not a simple ion exchange process, because the magnesium ions are substantially not released from the ion exchange medium into the onium hydroxide and/or salt solution being purified (if this was the case, the resulting onium hydroxide and/or salt solution would still contain unwanted ions). Although not to be bound by theory, it is thought that in one embodiment, the metal ions dissolved in the onium hydroxide and/or salt solution form a complex with the magnesium ions on the ion exchange medium as the onium hydroxide and/or salt solution is passed through the ion exchange medium in accordance with the present invention.

As discussed in the background section, standard, previously known processes for recycling onium hydroxide and/or salt solutions have not been able to attain the desired purity; and in particular have not been able to attain the desired removal of metal ions. In some cases, recycled onium hydroxide and/or salt solutions contain metals in excess of 100 parts per million (ppm). In some cases, lower levels have been attained. Thus, in one embodiment, the onium hydroxide and/or salt solution to be treated in the process of the present invention contains from about 0.1 to about 100 part per million of metal ions prior to passing the solution through the ion exchange medium. In another embodiment, the onium hydroxide and/or salt solution to be treated in the process of the present invention contains from about 1 to about 10 ppm of metal ions prior to the treatment. In other embodiments, the metal content may be lower or higher. Thus, for example, the onium hydroxide and/or salt solution to be treated may contain an amount greater than allowed by the specifications required for metal content, e.g., greater than about 1 ppb of aluminum. It is noted that, in some embodiments, it is more efficient to employ other standard recycling processes to remove the bulk of the metal ions prior to use of the process of the present invention to remove the metal ions to attain the low levels obtainable herein. In one embodiment, the onium hydroxide and/or salt solution to be treated in the present process is pre-treated to remove metal ions and metal-containing particles down to a content in the range from about 0.1 to about 100 ppm.

As noted, in one embodiment, the present invention can attain a substantial reduction in the metal ion content of the subject onium hydroxide and/or salt solutions. Thus, in one embodiment, the onium hydroxide and/or salt solution collected in the process of the present invention comprises about 1 part per billion or less of metal ions. In one embodiment, the onium hydroxide and/or salt solution collected comprises about 0.1 part per billion or less of metal ions. In one embodiment, metal ions are not detectable by standard, currently available analytical techniques in the onium hydroxide and/or salt solution collected from the process of the present invention.

In one embodiment, the onium hydroxide and/or salt solution to be treated by the present process contains no suspended particles, in particular, no suspended particles of metal-containing materials. Thus, in one embodiment, the present invention is not for the purpose of removing suspended particles, e.g., turbidity due to fine particles of metal oxides or other metal compounds. In one embodiment, the present invention can remove such turbidity, but it is primarily for the purpose of removing dissolved metal ions down to the indicated levels.

In one embodiment, the onium hydroxide and/or salt solution comprises tetramethylammonium hydroxide (TMAH) or a TMA salt, and in one embodiment, the onium hydroxide and/or salt solution consists essentially of tetramethylammonium hydroxide and/or salt; that is, in such an embodiment, the onium hydroxide and/or salt in the onium hydroxide and/or salt solution is tetramethylammonium hydroxide and/or salt, although the onium hydroxide and/or salt solution may comprise other ingredients. At present, TMAH is widely used in the semiconductor industry as a resist developer and as an alkaline etchant.

Thus, in one embodiment of the present invention, a process is provided for recycling a recovered TMAH solution containing dissolved metal ions, comprising:

providing a weak acid ion exchange medium;

providing a solution comprising magnesium ions;

forming a magnesium-loaded ion exchange medium by contacting the ion exchange medium with the solution comprising magnesium ions;

contacting the magnesium-loaded ion exchange medium with a recovered tetramethylammonium hydroxide and/or salt solution containing a first quantity of dissolved metal ions, wherein at least a portion of the dissolved metal ions are removed from the tetramethylammonium hydroxide and/or salt solution; and collecting a tetramethylammonium hydroxide and/or salt solution, wherein the collected solution contains a second quantity of dissolved metal ions smaller than the first quantity. As described, in this embodiment, the cycled onium hydroxide and/or salt is a TMAH or TMA salt solution. The TMAH or TMA salt solution initially provided for processing contains a first quantity of dissolved metal ions and, as a result of the process of this embodiment, the first quantity is reduced to a second, lower quantity, and in one embodiment, the second lower quantity is sufficiently low to satisfy semiconductor industry specifications for dissolved metal content.

In one embodiment, the ion exchange medium is loaded onto a column and in the forming step the solution comprising magnesium ions is passed through the column in a first direction and in the contacting the recovered tetramethylammonium hydroxide and/or salt solution is passed through the column in a second direction opposite to the first direction.

In one embodiment, the column is rinsed by passing a substantially metal-free tetramethylammonium hydroxide and/or salt solution over the ion exchange medium after the ion exchange medium is contacted with the solution comprising magnesium ions and prior to the contacting with the recovered tetramethylammonium hydroxide and/or salt solution.

In another embodiment, the process for recycling a recovered tetramethylammonium hydroxide and/or salt solution containing dissolved metal ions includes:

providing a carboxylate weak acid ion exchange medium and loading the ion exchange medium onto a column;

providing a solution comprising magnesium ions;

forming a magnesium-loaded ion exchange medium by contacting the ion exchange medium with the solution comprising magnesium ion, wherein the solution comprising magnesium ions passes through the column in a first direction;

rinsing the ion exchange medium by contacting the magnesium-loaded ion exchange medium with a substantially metal-free tetramethylammonium hydroxide and/or salt solution, wherein the substantially metal-free tetramethylammonium hydroxide and/or salt solution passes through the column in a second direction opposite to the first direction;

contacting the rinsed magnesium-loaded ion exchange medium with the recovered tetramethylammonium hydroxide and/or salt solution, wherein the recovered tetramethylammonium hydroxide and/or salt solution passes through the column in the second direction, wherein at least a portion of the dissolved metal ions are retained on the ion exchange medium; and collecting the tetramethylammonium hydroxide and/or salt solution after the contacting, wherein the solution collected contains a reduced quantity of dissolved metal ions. As described, in this embodiment, the cycled onium hydroxide and/or salt is a TMAH or TMA salt solution. The TMAH or TMA salt solution initially provided for processing contains a first quantity of dissolved metal ions and, as a result of the process of this embodiment, the first quantity is reduced to a second, lower quantity, and in one embodiment, the second lower quantity is sufficiently low to satisfy semiconductor industry specifications for dissolved metal content.

As discussed above, in some embodiments, the recovered tetramethylammonium hydroxide and/or salt solution contains from about 0.1 to about 100 part per million of metal prior to the treatment, and in some embodiments, the collected tetramethylammonium hydroxide and/or salt solution comprises about 1 part per billion or less of metal ions, and in some embodiments, less than 0.1 ppb of metal ions.

Exemplary Procedure:

The following is an exemplary process for carrying out an embodiment of the present invention, and is provided for exemplary, non-limiting purposes.

| Resin: | CNP-80 Bayer AG |
|---|---|
| Column: | PFA column, vertically oriented |
| | Diameter: 2.5 cm |
| | Bed Height: 50 cm. |
| | Bed Volume: 245 cm$^3$ |

Magnesium Hydroxide:

32 g. Mg(OH)$_2$ is added to 2 liters of water and mixed with magnetic stirrer, forming a slurry of magnesium hydroxide. The slurry is circulated through a filter into the column in an upflow at 30-50 ml/minute until the slurry becomes clear.

Pure TMAH Wash:

Following the deposition of magnesium hydroxide on the column, 500 ml of a 15% solution of pure, metal-free TMAH is passed through the column in an upflow direction at 2 ml/min to wash the column and condition it for the recycled TMAH which is to be treated.

Metal Removal Examples:

Aliquots from several different solutions of recovered (recycled) TMAH are treated by passing each through a weak acid ion exchange column, prepared as above, at a flow rate of about 125 ml/hour (about 2 ml/min), which is about 0.5 SV (specific volume of the column) per hour. Two columns are prepared as described above. The same column was used for all the samples shown in each of the two sets of results below in Tables 1 and 2, without regeneration between successive samples in each respective set.

Results:

Table 1 shows, for a first column set up as described above, the sample identification, the volume of each sample introduced into the column, the cumulative total volume in each set of samples passed through the column, the TMAH assay, the metal concentrations before and after passing through the column. As is clearly apparent, the method of the present invention efficiently removes metals from the recovered or recycled TMAH solutions, to provide a purified TMAH useable in, e.g., processing of semiconductors, substantially equivalent to new, pure, metal-free TMAH.

Table 2 shows, for a second column set up as described above, the sample identification, the volume of each sample introduced into the column, the cumulative total volume in each set of samples passed through the column, the TMAH assay, the metal concentrations before and after passing through the column. As is clearly apparent, the method of the present invention efficiently removes metals from the recovered or recycled TMAH solutions, to provide a purified TMAH useable in, e.g., processing of semiconductors, substantially equivalent to new, pure, metal-free TMAH.

TABLE 1

| | Volume, ml | | TMAH | Initial Metal Concentration, ppb | | | | Post-Treat Metal Concentration, ppb | | | |
|---|---|---|---|---|---|---|---|---|---|---|---|
| Sample | Sample | Cumulative | wt. % | Al | Fe | Zn | Na | Al | Fe | Zn | Na |
| FW 2P | 732 | 732 | 15.12 | 50 | — | 50 | 2 | 1.9 | | | |
| FW 3P + FW 4P | 2200 | 2932 | 15.38 | 90 | 250 | 50 | 8 | <0.5 | 2.8 | | |
| | | | 15.67 | 200 | 350 | 80 | 14 | | | | |
| FW 5P | 1300 | 4232 | 15.01 | 150 | 230 | 100 | 18 | <0.5 | 2 | | |
| FW 6P | 1000 | 5232 | 14.33 | 340 | 190 | 80 | 9 | <0.5 | 2.4 | | |
| FW 7P | 1000 | 6232 | 15.49 | 90 | 170 | 170 | 5 | 0.9 | 6.3 | | |
| FW 7P + NW 1P | 865 | 7097 | 15.49 | 90 | 170 | 10 | 4 | 0.3 | 0.8 | | |
| | | | 10.27 | 2400 | 160 | 170 | 5 | | | | |
| NW 2P | 916 | 8012 | 14.08 | >3500 | 150 | 50 | 200 | 0.5 | 2.7 | | |
| YW 1P | 550 | 8563 | 11.38 | 180 | 220 | 90 | 29 | 0.8 | 11 | | |
| FW 3P | 1000 | 9563 | 15.38 | 90 | 350 | 50 | 2 | 0.3 | 0.6 | | |
| FR 10P | 1039 | 10602 | 14.9 | 1400 | 150 | 160 | 12 | 0.5 | 3.3 | | |
| FR 4P | 805.5 | 11407.5 | 14.75 | 400 | 80 | 80 | 1 | 0.4 | 0.2 | | |
| FR 2P | 230 | 11637.5 | 16.32 | 630 | 170 | 100 | 17 | 0.7 | 2.2 | | |
| S2R 1P | 650 | 12287.5 | 12.6 | >3900 | 540 | 270 | 67 | <0.5 | 0.6 | >11 | 67 |
| S2R 3P | 1166 | 13453.5 | 11 | >6400 | 570 | 1000 | 20 | 0.7 | | | |

TABLE 2

| | Volume, ml | | TMAH | Initial Metal Concentration, ppb | | | | Post-Treat Metal Concentration, ppb | | | |
|---|---|---|---|---|---|---|---|---|---|---|---|
| Sample | Sample | Cumulative | wt. % | Al | Fe | Zn | Na | Al | Fe | Zn | Na |
| MPR P1 | 550 | 550 | 12.43 | 500 | 70 | 10 | 2 | 0.9 | 1.4 | 0.3 | 29 |
| MPR P2 | 872 | 1422 | 13.33 | >330 | 73 | 3.8 | 1.2 | 0.8 | 73 | 3.8 | 1.2 |
| MPR P3 | 970 | 2392 | 14.54 | 2000 | 60 | 20 | 2.3 | <5* | <5* | 3 | 4 |
| MPR P4 | 1055 | 3447 | 13.25 | >3000 | 52 | 9 | 7 | <5* | <5* | 2 | 3 |
| MPR P5 | 1570 | 5017 | 15.14 | 4400 | 57 | 53 | 2 | <5* | <5* | 18-32 | 3-4 |
| MPR P6 | 1190 | 6307 | 15.08 | 830 | 100 | 50 | 20 | <5* | <5* | 50 | 3 |
| SCR 3-3 | 1000 | 7207 | 20.99 | 40 | 260 | 30 | 4200 | 0.2 | | | |

*"<5*" reflects that the samples were diluted for analysis, so the detection limit is higher

COMPARATIVE EXAMPLES

The following comparative examples are provided to demonstrate the efficacy of the weak acid ion exchange media as distinct from either strong acid ion exchange media or chelate ion exchange media.

| Strong Acid Cation Exchange Resin | |
|---|---|
| Resin: | DIAION ® SK1B Mitsubishi |
| Column: | PFA column, vertically oriented |
| | Diameter: 2 cm |
| | Bed Height: 40 cm. |
| | Bed Volume: 125.7 cm$^3$ |

Magnesium Hydroxide:

400 ml of 5% $MgSO_4 \cdot 7H_2O$ in water is charged into the column at SV=2, which is equivalent to 250 ml/hour. After washing with a pure, metal-free 15% solution of TMAH as described above, a 15% solution of TMAH containing 10 ppm aluminum is charged to the column at SV=1. The following results are obtained:

| Fraction | Volume | Al, ppm |
|---|---|---|
| 1 | 275 ml | 5 |
| 2 | 275 ml | 6 |
| 3 | 275 ml | 7 |
| 4 | 275 ml | 5 |
| 5 | 275 ml | 7 |

(Note that the Al concentration is in ppm, not ppb).

| Chelate Resin | |
|---|---|
| Resin: | AMBERLITE ® IRC747 Rohm & Haas |
| Column: | PFA column, vertically oriented |
| | Diameter: 2 cm |

Preparation:

A slurry/solution of 500 ml water containing 10 g. $Mg(OH)_2$ is mixed with 65 ml of the IRC747 resin, and mixed in a rotary evaporator until the turbidity of the slurry/solution becomes almost clear. The combined resin and slurry/solution is charged into the column and rinsed with a pure, metal-free 15% TMAH solution as described above.

A solution containing 15% TMAH and 1000 ppb (1 ppm) of aluminum is charged into the column at SV=1. The following results are obtained:

| Fraction | Volume | Al, ppb |
|---|---|---|
| 1 | 252 ml | 220 |
| 2 | 270 ml | 350 |
| 3 | 250 ml | 240 |
| 4 | 275 ml | 300 |
| 5 | 155 ml | 900 |
| 6 | 270 ml | 730 |
| 7 | 175 ml | 560 |
| 8 | 250 ml | 60 |
| 9 | 97 ml | 160 |
| 10 | 152 ml | 330 |
| 11 | 190 ml | 490 |

| Weak Acid Ion Exchange Resin (according to the present invention) | |
|---|---|
| Resin: | CNP-80 Bayer AG |
| Column: | PFA column, vertically oriented |
| | Diameter: 2.2 cm |
| | Bed Volume: about 74 cm$^3$ |

Preparation:

74 ml of the resin is charged into the column. A slurry/solution of 1000 ml water containing 14 g. $Mg(OH)_2$ is passed through the column until the turbidity of the slurry/solution becomes almost clear. The combined resin and slurry/solution is rinsed with a pure, metal-free 15% TMAH solution as described above.

Eleven liters of a solution containing 15% TMAH and 1000 ppb (1 ppm) of aluminum is charged into the column at SV=1. The aluminum concentration of the effluent is less than 10 ppb for the 11 liters.

A further 10 liters of recovered 18.5% TMAH solution containing 520 ppb of aluminum is passed through the column at SV=1. The aluminum concentration of the effluent is less than 2 ppb for the 10 liters.

Medium Regeneration

In one embodiment, the weak acid ion exchange medium is regenerated as needed. In one embodiment, "as needed" is determined by the "break-through" point of metal ions, that is, when the treated onium hydroxide and/or salt solution obtained as the effluent from the column begins to show an increase in the metal ion content, the "break-through" point has been reached and the column is regenerated. In other embodiments, the time at which the weak acid ion exchange medium is regenerated is determined based on other criteria determined by the operator, such as by calculation of the total quantity of metal theoretically deposited onto the column by repeated treatments of onium hydroxide and/or salt solutions having known or estimated loadings of dissolved metal ions to be removed.

In one embodiment, the weak acid ion exchange medium is regenerated by treatment with a suitable acid solution. The acid solution regenerates the column by removing metal ions, including the magnesium ions used to initially prepare the column. In one embodiment, the weak acid ion exchange medium is regenerated by treatment with a solution of one or more of hydrochloric acid, sulfuric acid, sulfamic acid, sulfonic acid, phosphoric acid or nitric acid. In one embodiment, the acid is hydrochloric acid. In one embodiment, the acid concentration ranges from about 1 to about 10 percent by volume, and in another embodiment from about 3 to about 5 percent by volume. The amount of acid used to regenerate the column, in one embodiment, ranges from about 1.5 to about 4 times the calculated equivalent weak acid content of the column, and in one embodiment, from about 1.5 to about 2 times the calculated equivalent weak acid content of the column. That is, the amount of acid used is determined based on the calculated number of weak acid groups based on the type and quantity of resin packed in the column. For regeneration, the acid solution used for the regeneration may be passed through the column at rates up to SV=4 or SV=5. Higher or lower rates may be used, although the efficiency of the regeneration may be reduced.

In one embodiment, the weak acid ion exchange medium is simply discarded subsequent to its use in accordance with the present invention. In another embodiment, the weak acid ion exchange medium is regenerated subsequent to its use in accordance with the present invention, but after the regeneration is used for other, less demanding, applications than as described in the present invention.

While the invention has been explained in relation to certain of its exemplary embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for removing dissolved metal ions from an onium hydroxide and/or salt solution, comprising:
   providing a weak acid ion exchange medium;
   providing a solution comprising magnesium ions;
   forming a magnesium-loaded ion exchange medium by contacting the ion exchange medium with the solution comprising magnesium ions;
   contacting the magnesium-loaded ion exchange medium with an onium hydroxide and/or salt solution containing a first quantity of dissolved metal ions, wherein at least a portion of the dissolved metal ions are removed from the onium hydroxide and/or salt solution; and
   collecting the onium hydroxide and/or salt solution after the contacting, wherein the solution collected contains a second quantity of dissolved metal ions smaller than the first quantity.

2. The process of claim 1 further comprising loading the ion exchange medium onto a column.

3. The process of claim 1 wherein the step of providing a solution comprising magnesium ions comprises dissolving MgO and/or Mg(OH)$_2$ in water.

4. The process of claim 1 wherein a quantity of magnesium ions loaded onto the ion exchange medium is substantially stoichiometric with available acid sites on the ion exchange medium.

5. The process of claim 1 wherein the onium hydroxide and/or salt solution comprises from about 0.1 to about 100 parts per million of metal ions prior to contacting the magnesium-loaded ion exchange medium with the onium hydroxide and/or salt solution.

6. The process of claim 1 wherein the collected onium hydroxide and/or salt solution comprises about 1 part per billion or less of metal ions.

7. The process of claim 1 wherein the onium hydroxide and/or salt solution comprises an ammonium hydroxide and/or salt.

8. The process of claim 7 wherein the ammonium hydroxide and/or salt comprises a tetraalkylammonium hydroxide and/or salt.

9. The process of claim 8 wherein the alkyl groups comprise methyl groups.

10. The process of claim 1 wherein the ion exchange medium is loaded onto a column and in the forming the solution comprising magnesium ions is passed through the column in a first direction and in the contacting the onium hydroxide and/or salt solution is passed through the column in a second direction opposite to the first direction.

11. The process of claim 10 further comprising passing a substantially metal-free onium hydroxide and/or salt solution over the ion exchange medium after the solution comprising magnesium ions is passed through the ion exchange medium and prior to the contacting with the onium hydroxide and/or salt solution.

12. The process of claim 11 wherein the substantially metal-free onium hydroxide and/or salt contains about 1 part per billion or less of metal.

13. The process of claim 1 wherein the ion exchange resin comprises carboxylate groups as active ion exchange moieties.

14. The process of claim 1 wherein the metal ion includes aluminum, iron and zinc, and alloys or mixtures of any two or more of these.

15. The process of claim 1 wherein the metal ion includes aluminum, barium, bismuth, boron, cadmium, calcium, cerium, copper, germanium, hafnium, iron, lanthanum, lead, nickel, niobium, scandium, silicon, strontium, titanium, tungsten, yttrium, zinc, zirconium, and alloys or mixtures of any two or more of these.

16. A process for recycling a recovered tetramethylammonium hydroxide and/or salt solution containing dissolved metal ions, comprising:
   providing a weak acid ion exchange medium;
   providing a solution comprising magnesium ions;
   forming a magnesium-loaded ion exchange medium by contacting the ion exchange medium with the solution comprising magnesium ions;
   contacting the magnesium-loaded ion exchange medium with a recovered tetramethylammonium hydroxide and/or salt solution containing a first quantity of dissolved metal ions, wherein at least a portion of the dissolved metal ions are removed from the tetramethylammonium hydroxide and/or salt solution; and
   collecting a tetramethylammonium hydroxide and/or salt solution, wherein the collected solution contains a second quantity of dissolved metal ions smaller than the first quantity.

17. The process of claim 16 further comprising loading the ion exchange medium onto a column.

18. The process of claim 16 wherein the step of providing a solution comprising magnesium ions comprises dissolving MgO and/or Mg(OH)$_2$ in water.

19. The process of claim 16 wherein a quantity of magnesium ions loaded onto the ion exchange medium is substantially stoichiometric with available acid sites on the ion exchange medium.

20. The process of claim 16 wherein the recovered tetramethylammonium hydroxide and/or salt solution comprises from about 0.1 to about 100 part per million of metal prior to contacting the magnesium-loaded ion exchange medium with the recovered tetramethylammonium hydroxide and/or salt solution.

21. The process of claim 16 wherein the collected tetramethylammonium hydroxide and/or salt solution comprises about 1 part per billion or less of metal subsequent to passing the solution through the ion exchange medium.

22. The process of claim 16 wherein the ion exchange medium is loaded onto a column and in the forming the solution comprising magnesium ions is passed through the column in a first direction and in the contacting the recovered tetramethylammonium hydroxide and/or salt solution is passed through the column in a second direction opposite to the first direction.

23. The process of claim 16 further comprising passing substantially metal-free tetramethylammonium hydroxide and/or salt solution over the ion exchange medium after the solution comprising magnesium ions is passed through the ion exchange medium and prior to the contacting with the recovered tetramethylammonium hydroxide and/or salt solution.

24. The process of claim 23 wherein the substantially metal-free tetramethylammonium hydroxide and/or salt contains about 1 part per billion or less of metal.

25. The process of claim 16 wherein the ion exchange resin comprises carboxylate groups as active ion exchange moieties.

26. The process of claim 16 wherein the metal ion includes aluminum, iron and zinc, and alloys or mixtures of any two or more of these.

27. The process of claim 16 wherein the metal ion includes aluminum, barium, bismuth, boron, cadmium, calcium, cerium, copper, germanium, hafnium, iron, lanthanum, lead, nickel, niobium, scandium, silicon, strontium, titanium, tungsten, yttrium, zinc, zirconium, and alloys or mixtures of any two or more of these.

28. A process for recycling a recovered tetramethylammonium hydroxide and/or salt solution containing dissolved metal ions, comprising:
providing a carboxylate weak acid ion exchange medium and loading the ion exchange medium onto a column;
providing a solution comprising magnesium ions;
forming a magnesium-loaded ion exchange medium by contacting the ion exchange medium with the solution comprising magnesium ions, wherein the solution comprising magnesium ions passes through the column in a first direction;
rinsing the ion exchange medium by contacting the magnesium-loaded ion exchange medium with a substantially metal-free tetramethylammonium hydroxide and/or salt solution, wherein the substantially metal-free tetramethylammonium hydroxide and/or salt solution passes through the column in a second direction opposite to the first direction;
contacting the rinsed magnesium-loaded ion exchange medium with the recovered tetramethylammonium hydroxide and/or salt solution, wherein the recovered tetramethylammonium hydroxide and/or salt solution passes through the column in the second direction, wherein at least a portion of the dissolved metal ions are retained on the ion exchange medium; and
collecting the tetramethylammonium hydroxide and/or salt solution after the contacting, wherein the collected tetramethylammonium hydroxide and/or salt solution contains a reduced quantity of dissolved metal ions.

29. The process of claim 28 wherein a quantity of magnesium ions loaded onto the ion exchange medium is substantially stoichiometric with available carboxylate sites on the ion exchange medium.

30. The process of claim 28 wherein the recovered tetramethylammonium hydroxide and/or salt solution comprises from about 0.1 to about 100 part per million of metal prior to contacting the magnesium-loaded ion exchange medium with the recovered tetramethylammonium hydroxide and/or salt solution.

31. The process of claim 28 wherein the collected tetramethylammonium hydroxide and/or salt solution comprises about 1 part per billion or less of metal.

32. The process of claim 28 wherein the metal ion includes aluminum, iron and zinc, and alloys or mixtures of any two or more of these.

33. The process of claim 28 wherein the metal ion includes aluminum, barium, bismuth, boron, cadmium, calcium, cerium, copper, germanium, hafnium, iron, lanthanum, lead, nickel, niobium, scandium, silicon, strontium, titanium, tungsten, yttrium, zinc, zirconium, and alloys or mixtures of any two or more of these.

* * * * *